United States Patent
Dziekonski et al.

(10) Patent No.: US 12,064,501 B2
(45) Date of Patent: Aug. 20, 2024

(54) PERSONAL CARE COMPOSITIONS

(71) Applicant: Colgate-Palmolive Company, New York, NY (US)

(72) Inventors: Dariusz Dziekonski, Lawrenceville, NJ (US); Tochukwu Ofoegbuna, New Brunswick, NJ (US); Hrebesh Molly Subhash, Somerset, NJ (US); Shyamala Pillai, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 18/297,135

(22) Filed: Apr. 7, 2023

(65) Prior Publication Data

US 2023/0320952 A1 Oct. 12, 2023

Related U.S. Application Data

(60) Provisional application No. 63/328,456, filed on Apr. 7, 2022.

(51) Int. Cl.

| | |
|---|---|
| *A61K 8/29* | (2006.01) |
| *A61K 8/19* | (2006.01) |
| *A61K 8/27* | (2006.01) |
| *A61K 8/28* | (2006.01) |
| *A61K 8/31* | (2006.01) |
| *A61K 8/33* | (2006.01) |
| *A61K 8/34* | (2006.01) |
| *A61K 8/36* | (2006.01) |
| *A61K 8/37* | (2006.01) |
| *A61Q 5/02* | (2006.01) |
| *A61Q 5/12* | (2006.01) |
| *A61Q 15/00* | (2006.01) |
| *A61Q 19/00* | (2006.01) |
| *A61Q 19/10* | (2006.01) |

(52) U.S. Cl.
CPC .......... *A61K 8/29* (2013.01); *A61K 8/19* (2013.01); *A61K 8/31* (2013.01); *A61K 8/33* (2013.01); *A61K 8/345* (2013.01); *A61K 8/36* (2013.01); *A61K 8/37* (2013.01); *A61Q 5/02* (2013.01); *A61Q 5/12* (2013.01); *A61Q 15/00* (2013.01); *A61Q 19/00* (2013.01); *A61Q 19/10* (2013.01); *A61K 8/27* (2013.01); *A61K 8/28* (2013.01); *A61K 2800/30* (2013.01); *A61K 2800/58* (2013.01)

(58) Field of Classification Search
None
See application file for complete search history.

(56) References Cited

U.S. PATENT DOCUMENTS

| | | | |
|---|---|---|---|
| 6,007,799 A | 12/1999 | Lee et al. | |
| 6,479,036 B1 * | 11/2002 | Stanier | A61K 8/25 106/272 |
| 8,603,442 B2 | 12/2013 | Sharma | |
| 8,632,754 B2 | 1/2014 | Sharma | |
| 9,301,935 B2 | 4/2016 | Uddin | |
| 9,561,193 B2 | 2/2017 | Subramanyam | |
| 9,682,256 B2 | 6/2017 | Boyd | |
| 11,058,904 B2 | 7/2021 | Misner et al. | |
| 2011/0027196 A1 * | 2/2011 | Sharma | A61Q 11/00 424/49 |
| 2016/0067170 A1 * | 3/2016 | Welss | A61K 8/4953 424/401 |
| 2016/0206534 A1 * | 7/2016 | Banowski | A61K 8/365 |
| 2016/0296428 A1 * | 10/2016 | Anconi | A61K 8/26 |
| 2017/0312301 A1 | 11/2017 | Saeki | |
| 2019/0185339 A1 * | 6/2019 | Dubovoy | C01G 25/04 |
| 2020/0368123 A1 * | 11/2020 | Soliman | A61K 8/25 |
| 2022/0008371 A1 | 1/2022 | Uddin | |
| 2022/0168195 A1 * | 6/2022 | Liu | A61K 8/20 |

FOREIGN PATENT DOCUMENTS

| | | |
|---|---|---|
| EP | 2281548 | 2/2011 |
| WO | 1994/015574 | 7/1994 |
| WO | 1996/036324 | 11/1996 |
| WO | WO-2021260202 A1 * | 12/2021 |

OTHER PUBLICATIONS

Norwex ("Norwex® Introduces New Prebiotic Deodorant and Moisture-Rich Body Lotion to LysereTM Personal Care Collection"), obtained from: https://www.prnewswire.com/news-releases/norwex-introduces-new-prebiotic-deodorant-and-moisture-rich-body-lotion-to-lysere-personal-care-collection-301387407.html). (Year: 2021).*

"Xanthan Gum" (an internet article obtained from the website: https://www.cosmeticsinfo.org/ingredients/xanthan-gum/ ). (Year: 2021).*

International Search Report and the Written Opinion of the International Searching Authority issued in International Application PCT/US2023/017840 mailed Aug. 24, 2023.

\* cited by examiner

*Primary Examiner* — Sin J Lee

(57) ABSTRACT

The application relates to personal care products (e.g., deodorants and/or antiperspirants) that can provide a sweat reduction effect without the use of aluminum salts. In one aspect, the compositions comprise a metal oxalate (i.e., potassium oxalate or potassium titanium oxalate). Methods of preparing the personal care composition and uses of the personal care composition are also disclosed.

19 Claims, 1 Drawing Sheet

Baseline      t = 0.5 h      t = 2 h

Baseline      t = 0.5 h      t = 2 h

PERSONAL CARE COMPOSITIONS

CROSS-REFERENCE TO RELATED APPLICATION

This application claims the benefit of priority from U.S. Provisional Application No. 63/328,456, filed on Apr. 7, 2022, the contents of which are hereby incorporated herein in their entirety for all purposes.

FIELD OF DISCLOSURE

The application relates to personal care products (e.g., deodorants and/or antiperspirants) that can provide a sweat reduction effect without the use of aluminum salts. In one aspect, the personal care compositions comprise a metal oxalate (i.e., potassium oxalate or potassium titanium oxide oxalate). Methods of preparing the personal care composition and uses of the personal care composition are also disclosed.

BACKGROUND

Personal care compositions, such as antiperspirant or deodorant compositions and dual purpose antiperspirant-deodorant compositions, may be used to reduce body odor. Antiperspirant or deodorant compositions may be applied to axillary (underarm) regions to prevent or treat perspiration, limit the growth of odor-causing bacteria, or apply a fragrance. Antiperspirant or deodorant compositions may be delivered topically as roll-on, gel, cream, stick or aerosol formulations. Underarm deodorants and antiperspirants control odor by eliminating the bacteria that cause odor. Conventional antiperspirant salts, such as aluminum, and/or zirconium salts, tend to be acidic in aqueous solution, a property which makes them effective bactericides, thereby providing a deodorant benefit, but which can also cause skin irritation. In addition, long-acting antiperspirant compositions typically contain increased amounts of active ingredients as a route to obtaining sustained effectiveness. At the same time, skin sensitivity and vulnerability to various compounds may limit the practical upper concentration in personal care formulations. It is now believed that a relatively large percent of the population may have sensitive skin with a reduced irritation threshold.

Generally, aluminum salts are the active ingredients of antiperspirant products. Without being bound by theory, their mechanism of action involves a temporary plugging of sweat pores, thereby blocking sweat and providing a sweat reduction attribute. In recent years there has been increasing consumer pressure to reduce or remove aluminum salts from antiperspirant or deodorant type products. However, replacing aluminum salts in antiperspirant and deodorant products, but at the same time maintaining the same desirable sweat blocking properties consumers value in an antiperspirant or deodorant product, is a challenge within the personal care composition industry.

Accordingly, there is an unmet need for personal care products that can provide the sweat and perspiration reduction qualities of products with aluminum salts but at the same time use an active other than aluminum compounds.

BRIEF SUMMARY

In one aspect, the application is directed to personal care products (e.g., deodorants and/or antiperspirants), wherein the personal care product contains a metal oxalate which acts as a replacement for aluminum salts (e.g., blends of aluminum chloride or aluminum zirconium). Without being bound by theory, the inclusion of a metal oxalate (e.g., potassium oxalate or potassium titanium oxide oxalate) in the formula reacts with calcium in a user's sweat in order to produce an insoluble precipitate (e.g., a mixture of calcium titanium oxalate and calcium oxalate) and temporarily blocks the sweat duct.

In one embodiment, the personal care composition comprises a metal oxalate and is free or substantially free of an aluminum antiperspirant agent/active. In this embodiment, the personal care composition comprising the metal oxalate (e.g., potassium oxalate or potassium titanium oxide oxalate) can perform at parity, with respect to sweat reduction, with traditional antiperspirants that contain aluminum salt actives.

In one embodiment, the personal care composition comprises a metal oxalate and is free or substantially free of an aluminum antiperspirant agent/active and further comprises a gum base. In this embodiment, the personal care composition comprising the metal oxalate (e.g., potassium oxalate or potassium titanium oxide oxalate) comprises a gum base (e.g., from 0.5%-5% by wt. of the total composition) (e.g., where the gum base comprises xanthan gum, sodium starch octenylsuccinate & hydroxypropyl starch phosphate).

In another embodiment, a method of delivering a metal oxalate and is free or substantially free of an aluminum containing antiperspirant agent/active, wherein the formula reacts calcium in a user's sweat in order to produce an insoluble precipitate that is able to block sweat glands and reduce or prevent sweat.

In addition to antiperspirants and/or deodorants, the disclosure also encompasses other personal care compositions for application to the skin, for example hand soaps or body washes, comprising a potentially irritating active ingredient and/or precursors thereof. The disclosure further provides methods of reducing sweat comprising applying the composition to skin, and methods of killing bacteria comprising contacting the bacteria with the composition.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

Unless otherwise specified, all percentages and amounts expressed herein and elsewhere in the specification should be understood to refer to percentages by weight relative to the total composition. Unless specified otherwise, the amounts given are based on the active weight of the material relative to the total composition.

DETAILED DESCRIPTION

Figure 1A:
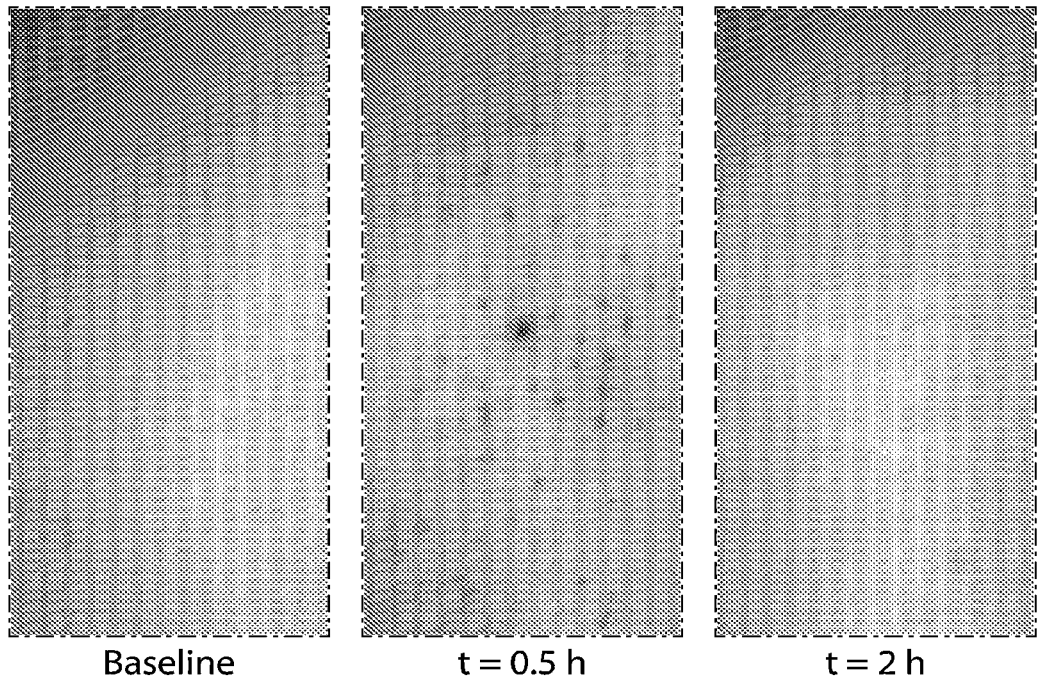
FIG. 1A is a thermal image demonstrating the visible pore activation on the skin from the application of a non-limiting, exemplary personal care composition containing potassium titanium oxalate ("KTO") in accordance with an aspect of the invention over a time course of two hours.

The following description of the preferred embodiment(s) is merely exemplary in nature and is in no way intended to limit the disclosure, its application, or uses.

The disclosure provides a personal care composition (Composition 1.0), which can be applied to the skin, as well as methods of reducing body odor and/or moisture comprising administering Composition 1.0 et seq to the skin.

The personal care composition may achieve the reduction of sweat while being free of or substantially free of certain traditional antiperspirant compositions, such as aluminum based antiperspirant actives, zirconium-based antiperspirant actives, zinc-based antiperspirant actives, iron-based antiperspirant actives, and/or magnesium-based antiperspirant actives. For example, the personal care compositions may have about 3 wt. % or less, about 2 wt. % or less, about 1 wt. % or less, about 0.5 wt. % or less, about 0.1 wt. % or less, about 0.05 wt. % or less, or about 0.01 wt. % or less of aluminum-based antiperspirant actives, magnesium-based antiperspirant actives, free-from zirconium-based antiperspirant actives, iron-based antiperspirant actives, and/or zinc-based antiperspirant actives (individually or cumulatively), based on the total weight of the personal care composition. In some embodiments, the personal care compositions have about 0 wt. % or 0 wt. % of aluminum-based antiperspirant actives, magnesium-based antiperspirant actives, zirconium-based antiperspirant actives, and/or zinc-based antiperspirant actives. In some embodiments, the personal care composition may, additionally or alternatively, be free of non-oxalate titanium-based antiperspirant actives, such as ammonium titanium lactate. For example, the personal care composition may comprise about 3 wt. % or less, about 2 wt. % or less, about 1 wt. % or less, about 0.5 wt. % or less, about 0.1 wt. % or less, about 0.05 wt. % or less, or about 0.01 wt. % or less of non-oxalate titanium-based antiperspirant actives.

The personal care compositions may be free of non-oxalate zinc-based antiperspirant actives and/or non-oxalate zirconium-based antiperspirant actives. For instance, the personal care composition may comprise about 3 wt. % or less, about 2 wt. % or less, about 1 wt. % or less, about 0.5 wt. % or less, about 0.1 wt. % or less, about 0.05 wt. % or less, or about 0.01 wt. % or less of non-oxalate zinc-based antiperspirant actives and/or non-oxalate zirconium-based antiperspirant actives, individually or cumulatively.

As used herein, the term "free of aluminum-based antiperspirant actives", means that the personal care compositions of the present disclosure do not comprise one or more of aluminum-based antiperspirant actives. Aluminum-based antiperspirant actives are not added to the personal care compositions of the invention to display some personal care effect.

As used herein, the term "aluminum free" or "free-from aluminum" means that the personal care composition does not contain any aluminum-based antiperspirant. Non limiting examples of aluminum-based antiperspirant actives, can include those listed in the US antiperspirant monograph, such as, aluminum chlorohydrate, aluminum chloride, aluminum dichlorohydrate, aluminum sesquichlorohydrate poylethylene glycol, aluminum sesquichlorohydrate propylene glycol, aluminum zirconium octachlorohydrate, aluminum zirconium pentachlorohydrate, aluminum zirconium tetrachlorohydrate, aluminum zirconium trichlorohydrate, aluminum sesquichlorohydrate, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex propylene glycol (aluminum chlorohydrex PG), aluminum chlorohydrex polyethylene glycol (aluminum chlorohydrex PEG), aluminum dichlorohydrex propylene glycol (aluminum dichlorohydrex PG), and aluminum dichlorohydrex polyethylene glycol (aluminum dichlorohydrex PEG).

As used herein, the term "zirconium free" or "free-from zirconium-based antiperspirant actives" means that the personal care composition does not contain any zirconium-based antiperspirant. The term "free of non-oxalate zirconium-based antiperspirant actives" means that the personal care composition does not comprise one or more of zirconium-based antiperspirant active other than zirconium containing oxalate based antiperspirant actives. Non-limiting examples of zirconium-based antiperspirant actives, include aluminum zirconium octachlorohydrate, aluminum zirconium pentachlorohydrate, aluminum zirconium tetrachlorohydrate, aluminum zirconium trichlorohydrate, and aluminum-zirconium glycine complex (e.g., aluminum zirconium trichlorohydrex gly, aluminum zirconium pentachlorohydrex gly, aluminum zirconium tetrachlorohydrex gly and aluminum zirconium octochlorohydrex gly).

As used herein, the term "free of zinc-based antiperspirant actives" means that the personal care composition does not comprise one or more of zinc-based antiperspirant actives. The term "free of non-oxalate zinc-based antiperspirant actives" means that the personal care composition does not comprise one or more of zinc-based antiperspirant active other than zinc containing oxalate based antiperspirant actives. Non-limiting examples of zinc-based antiperspirant actives can include one or more of zinc oxide, zinc hydroxide, zinc hydroxide ions with counter ions, and zinc ions with counter ions.

As used herein, the term "free of iron-based antiperspirant actives", means that the personal care composition does not comprise one or more of iron-based antiperspirant actives As used herein, the term "free of non-oxalate titanium-based antiperspirant actives" means that the personal care composition does not comprise one or more of titanium-based antiperspirant active other than titanium containing oxalate based antiperspirant actives, such as potassium titanium oxalate. For example, the personal care compositions may include a reduced amount, be substantially free of, or free of titanium-based antiperspirant actives, such as ammonium titanium lactate and the like.

As used herein, the term "free of magnesium-based antiperspirant actives", means that the personal care composition does not comprise one or more of magnesium-based antiperspirant actives. Non-limiting examples of magnesium-based actives include, but are not limited to, magnesium chloride, magnesium bromide, magnesium fluoride and organic salts such as various alkyl chain length substituted carboxylic acids, magnesium oxide, and magnesium hydroxide. As used herein, the term "axilla" or "axillary region" refers to the armpit or underarm of the body.

Additionally or alternatively, the personal care compositions may inhibit and/or reduce the growth of detrimental bacteria, responsible for the underarm malodor. Without being limited to any particular theory, it is believed that by reducing the underarm sweat, the personal care compositions may reduce the formation of the detrimental bacteria responsible for the malodor.

In another aspect, the disclosure provides Composition 1.0 (e.g., a stick deodorant or antiperspirant) for application to the skin. In one aspect, Composition 1.0 is a personal care composition that comprises a metal oxalate (e.g., potassium oxalate or potassium titanium oxide oxalate) (e.g., from about 0.5% to about 50 wt. %, by weight of the total personal care composition) (e.g., from 0.5 wt. % to 10 wt. %, by weight of the total personal care composition).

For example, Composition 1.0 also includes the following:

1.1 The personal care composition of Composition 1.0, wherein the metal in the metal oxalate comprises an alkali metal. The personal care composition typically comprises a antiperspirant component comprising one or more metal oxalate. In some embodiments, the antiperspirant component consists essentially of the one or more metal oxalate. In further embodiments, the antiperspirant component consists of the one or more metal oxalate. For example, the antiperspirant component may be comprised of about 20 wt. % or more of the one or more metal oxalate may comprise, based on the total weight of the antiperspirant component. In some instances, the antiperspirant component may be comprised of about 25 wt. % or more, about 35 wt. % or more, about 45 wt. % or more, about 55 wt. % or more, about 65 wt. % or more, about 75 wt. % or more, about 85 wt. % or more, about 90 wt. % or more, about 95 wt. % or more, about 98 wt. % or more of the one or more metal oxalate may comprise, based on the total weight of the antiperspirant component.

1.2 The personal care composition of Composition 1.0 or 1.1, wherein the alkali metal is selected from: Na, K, and Li.

1.3 The preceding composition, wherein the metal oxalate comprises potassium oxalate.

1.4 The personal care composition of Composition 1.0-1.3, wherein the metal oxalate comprises one or more metal oxides.

1.5 The preceding composition, wherein the metal in the metal oxalate is selected from the group consisting of: Ba, Ti, V, Cr, Mn, Fe, Co, Ni, Cu, Re, Os, Ir, Zn, Zr, Sn, and a combination of two or more thereof.

1.6 The preceding composition, wherein the metal oxalate comprises titanium oxide.

1.7 The personal care composition of any of Composition 1.0 to 1.6, wherein the composition comprises potassium oxalate and/or potassium titanium oxide oxalate (e.g., from 0.5 to 50 wt. %, by weight of the total personal care composition) (e.g., from 0.5 to about 10 wt. %, by weight of the total personal care composition).

1.8 The personal care composition of any of the preceding compositions wherein the metal oxalate is in the amount from 0.5 to 50 wt. %, by weight of the total personal care composition (e.g., from 0.5 to 50 wt. %, from about 5 to 50 wt. % from about 10 to 50 wt. %, from about 25 to 50 wt. % of potassium oxalate and/or potassium titanium oxalate, based on the total weight of the personal care composition). For instance, in some embodiments, the amount of metal oxalate present in the personal care composition is from about 1 to about 50 wt. %, about 10 to about 50 wt. %, about 15 to about 50 wt. %, about 20 to about 50 wt. %, about 25 to about 50 wt. %, about 30 to about 50 wt. %, about 35 to about 50 wt. %, about 40 to about 50 wt. %, about 45 to about 50 wt. %; from about 1 to about 45 wt. %, about 10 to about 45 wt. %, about 15 to about 45 wt. %, about 20 to about 45 wt. %, about 25 to about 45 wt. %, about 30 to about 45 wt. %, about 35 to about 45 wt. %, about 40 to about 45 wt. %; from about 1 to about 40 wt. %, about 10 to about 40 wt. %, about 15 to about 40 wt. %, about 20 to about 40 wt. %, about 25 to about 40 wt. %, about 30 to about 40 wt. %, about 35 to about 40 wt. %; from about 1 to about 35 wt. %, about 10 to about 35 wt. %, about 15 to about 35 wt. %, about 20 to about 35 wt. %, about 25 to about 35 wt. %, about 30 to about 35 wt. %; from about 1 to about 30 wt. %, about 10 to about 30 wt. %, about 15 to about 30 wt. %, about 20 to about 30 wt. %, about 25 to about 30 wt. %; from about 1 to about 25 wt. %, about 10 to about 25 wt. %, about 15 to about 25 wt. %, about 20 to about 25 wt. %; from about 1 to about 20 wt. %, about 10 to about 20 wt. %, about 15 to about 20 wt. %; from about 1 to about 15 wt. %, about 10 to about 15 wt. %, or any range or subrange thereof, based on the total weight of the personal care composition.

1.9 The personal care composition of any of the preceding compositions wherein the metal oxalate is in the amount from 0.5 to about 10 wt. %, by weight of the total personal care composition (e.g., from 0.5 to about 7.5 wt. %, from 0.5 to about 6 wt. %, about 1 wt. %, about 2 wt. %, about 3 wt. %, about 4 wt. %, or about 5 wt. % of potassium oxalate and/or potassium titanium oxalate, based on the total weight of the personal care composition). In some embodiment, the total amount of metal oxalate is from about 0.5 to about 11 wt. %, based on the total weight of the personal care composition. For instance, the metal oxalate may be present in the personal care composition in an amount from about 0.5 to about 11 wt. %, about 0.5 to about 9 wt. %, about 0.5 to about 7 wt. %, about 0.5 to about 5 wt. %, about 0.5 to about 4 wt. %, about 0.5 to about 3 wt. %, about 0.5 to about 2 wt. %, about 0.5 to about 1 wt. %; from about 1 to about 11 wt. %, about 1 to about 9 wt. %, about 1 to about 7 wt. %, about 1 to about 5 wt. %, about 1 to about 4 wt. %, about 1 to about 3 wt. %, about 1 to about 2 wt. %; from about 2 to about 11 wt. %, about 2 to about 9 wt. %, about 2 to about 7 wt. %, about 2 to about 5 wt. %, about 2 to about 4 wt. %, about 2 to about 3 wt. %; from about 3 to about 11 wt. %, about 3 to about 9 wt. %, about 3 to about 7 wt. %, about 3 to about 5 wt. %; from about 4 to about 11 wt. %, about 4 to about 9 wt. %, about 4 to about 7 wt. %, about 4 to about 6 wt. %, about 4 to about 5 wt. %; from about 5 to about 11 wt. %, about 5 to about 9 wt. %, about 5 to about 7 wt. %, about 5 to about 6 wt. %; from about 6 to about 11 wt. %, about 6 to about 9 wt. %, about 6 to about 8 wt. %, about 6 to about 7 wt. %; from about 7 to about 11 wt. %, about 7 to about 9 wt. %; from about 8 to about 11 wt. %, about 8 to about 10 wt. %, about 8 to about 9 wt. %, or about 9 to about 11 wt. %, or any range or subrange thereof, based on the total weight of the personal care composition.

1.10 The personal care composition of any of the preceding compositions, wherein the compositing further comprises one or more ingredient/component selected from the group consisting of: waxes, esters of fatty acid and fatty alcohol, triglycerides, partially or fully hydrogenated soybean oil, partially or fully hydrogenated castor oil, other partial or fully hydrogenated plant oils, or other cosmetically acceptable materials (e.g., which are solid or semi-solid at room temperature and provide a consistency suitable for application to the skin) and combinations thereof. The one or more foregoing ingredient may be a structuring agent and/or gelling agent. Examples of structuring agents include waxes and/or gelling agents.

1.11 Any of the preceding personal care compositions comprising a cosmetically acceptable base suitable for application to the skin, e.g., a cosmetically acceptable base comprising one or more of water-soluble alcohols (such as $C_{2-8}$ alcohols including ethanol; glycols (including propylene glycol, dipropylene glycol, tripropylene glycol and mixtures thereof); glycerides (including mono-, di- and triglycerides); medium to long chain organic acids, alcohols and esters (e.g., polyhydric alcohols) (e.g., butyloctanol); surfactants (including emulsifying and dispersing agents); additional amino acids; structurants (including thickeners and gelling agents, for example polymers, silicates (e.g., calcium silicate) and silicon dioxide); emollients; fragrances; colorants (including dyes and pigments), and combinations thereof.

1.12 Any of the preceding compositions, wherein the emollients, fragrances, colorants, structurants, thickeners, surfactants, glycerides, esters and alcohols are in an amount from 0.05 to 2 wt. % or 0.05 to 35 wt. %, by weight of the personal care composition.

1.13 Any of the preceding personal care compositions, further comprising an emollient selected from one or more of: glycerin, ethylhexyl glycerin, isododecane, sodium starch octenylsuccinate, $C_{12}$-$C_{15}$ alkyl benzoate, mineral oil, caprylyl glycol, dimethicone, dicaprylyl ether, ethyl trisiloxane, PPG-14 butyl ether, PPG-3 myristyl ether, secondary alcohol ethoxylates, stearyl alcohol, stearic acid and salts thereof, glyceryl monoricinoleate, isobutyl palmitate, isocetyl stearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl)adipate), Di-(2-ethyl hexyl)succinate, isopropyl myristate, isopropyl palmitate, isopropyl stearate, octacosanol, butyl stearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-8 distearate, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide, and combinations thereof.

1.14 Any of the preceding personal care compositions, further comprising a volatile emollient.

1.15 Any of the preceding personal care compositions, further comprising an antioxidant and/or preservative selected from citric acid, lactic acid, sodium benzoate, sodium lactate, triethyl citrate, butylated hydroxytoluene, and pentaerythrityl tetra-di-t-butyl hydroxyhydrocinnamate and combinations thereof.

1.16 The personal care composition of 1.15, wherein the antioxidant and/or preservative is present in an amount of 0.1 to 1% by wt. of the total composition.

1.17 Any of the preceding personal care compositions, further comprising one or more inert fillers (e.g., configured to give specific sensorial feelings to the antiperspirant composition when applied.).

1.18 The personal care composition of 1.17, wherein the inert filler is selected from: starches (e.g., hydroxypropyl starch phosphate, vegetable starches), talc, fumed silica and/or inorganic clays, polyethylene, and mixtures thereof.

1.19 Any of the preceding personal care compositions comprising a structuring agent, wherein the structuring agent is selected from the group consisting of: steareth-21, steareth-10, steareth-11, steareth-13, steareth-15, steareth-20, ceteareth-6, ceteareth-7, ceteareth-8, ceteareth-9, ceteareth-10, ceteareth-11, and ceteareth-12, polyglyceryl-6 palmitate/succinate mixture, glyceryl stearate, cetearyl alcohol (e.g., a 70/30 stearyl/cetyl alcohol blend), and combinations thereof.

1.20 Any of the preceding personal care compositions, wherein the personal care composition further comprises a prebiotic.

1.21 The preceding composition, wherein the prebiotic is selected from: inulin, glucose, fructose, sucrose and combinations thereof.

1.22 Any of the preceding personal care composition, wherein the personal care composition comprises one or more of: fragrances, preservatives, antioxidants, colorants and combinations thereof.

1.23 Any of the preceding personal care composition, wherein the personal care composition comprises one or more polyol.

1.24 Any of the preceding personal care compositions, wherein the personal care composition comprises a gum base.

1.25 The preceding personal care composition wherein the gum base comprises one or more of the following selected from xanthan gum, sodium starch octenylsuccinate, hydroxypropyl starch phosphate, diutan gum, carrageenan, carboxymethylcellulose, cellulose gum, sclerotium gum, hydroxypropyl methylcellulose, and combinations thereof.

1.26 Any of the preceding personal care compositions, wherein the personal care composition is in the form selected from: antiperspirants, deodorants, body washes, shower gels, bar soaps, shampoo, hair conditioners, and cosmetics.

1.27 The personal care composition of 1.24, wherein the personal care composition is an antiperspirant.

1.28 The personal care composition of any of the preceding compositions, wherein the composition is free or substantially free of an aluminum antiperspirant agent/active.

1.29 Any of the preceding personal care compositions, wherein the personal care composition (e.g., a roll-on antiperspirant) comprises:
  0.5%-7.5% by wt. of potassium titanium oxalate (e.g., about 1 wt. %, about 2 wt. %, about 3 wt. %, about 4 wt. %, about 5 wt. %, about 6 wt. %, or any range thereof, based on the total weight of the personal care composition);
  1%-20% by wt. of glycerin (e.g., about 5 wt. %, about 10 wt. %, about 15 wt. %, about 20 wt. %, or any range thereof, based on the total weight of the personal care composition); and
  0.5%-5% by wt. of isododecane (e.g., about 1 wt. %, about 2 wt. %, about 3 wt. %, about 4 wt. %, or any range thereof, based on the total weight of the personal care composition).

1.30 Any of the preceding personal care compositions, wherein the personal care composition (e.g., a roll-on antiperspirant) comprises:
- 0.5%-7.5% by wt. of potassium titanium oxalate (e.g., about 1 wt. %, about 2 wt. %, about 3 wt. %, about 4 wt. %, about 5 wt. %, about 6 wt. %, or any range thereof);
- 1%-20% by wt. of glycerin (e.g., about 5 wt. %, about 10 wt. %, about 15 wt. %, about 20 wt. %, or any range thereof, based on the total weight of the personal care composition);
- 0.5%-5% by wt. of isododecane (e.g., about 1 wt. %, about 2 wt. %, about 3 wt. %, about 4 wt. %, or any range thereof, based on the total weight of the personal care composition); and
- A gum blend base, wherein the gum blend comprises xanthan gum, sodium starch octenylsuccinate and hydroxypropyl starch phosphate.

1.31 Any of the preceding personal care compositions for use in forming an insoluble precipitate with the endogenous calcium in a user's skin in order to block sweat glands and reduce and/or prevent sweat or perspiration. The personal care compositions may provide a reduction of sweat of about 20% or more. For example, the personal care compositions may provide a reduction of sweat of about 20% or more in comparison to a personal care composition having the same formulation, expect that it includes additional carrier (e.g. water) instead of the metal oxalate. In certain embodiments, the personal care compositions provide a reduction of sweat of about 25% or more, about 35% or more, about 45% or more, about 50% or more, about 53% or more, about 59% or more, about 62% or more, about 64% or more, about 66% or more, about 68% or more, about 75% or more, about 80% or more, about 85% or more, about 90% or more, about 95% or more. For example, the personal care composition may provide reduction of sweat of about 25 to about 95%, about 35 to about 95%, about 45 to about 95%, about 55 to about 95%, about 55 to about 95%, about 65 to about 95%, about 70 to about 95%, about 75% to about 95%, about 80% to about 95%, about 85% to about 95%; from about 25 to about 85%, about 35 to about 85%, about 45 to about 85%, about 55 to about 85%, about 55 to about 85%, about 65 to about 85%, about 70 to about 85%, about 75% to about 85%, about 80% to about 85%; from about 25 to about 75%, about 35 to about 75%, about 45 to about 75%, about 55 to about 75%, about 55 to about 75%, about 65 to about 75%, about 70 to about 75%; from about 25 to about 70%, about 35 to about 70%, about 45 to about 70%, about 55 to about 70%, about 55 to about 70%, about 65 to about 70%; from about 25 to about 65%, about 35 to about 65%, about 45 to about 65%, about 55 to about 65%, about 55 to about 65%; from about 25 to about 60%, about 35 to about 60%, about 45 to about 60%, about 55 to about 60%, about 55 to about 60%; from about 25 to about 55%, about 35 to about 55%, about 45 to about 55%; from about 25 to about 50%, about 35 to about 50%, about 45 to about 50%; from about 25 to about 45%, about 35 to about 45%, or any range or subrange thereof. The reduction of sweat disclosed above may be achieved after, e.g., 2 hours of application and/or over a 24-hour period of application. The above reductions of sweat may in some embodiments be achieved in comparison to a personal care composition having the same formulation, expect that it includes additional carrier (e.g. water) instead of the metal oxalate.

1.32 Any of the preceding personal care compositions, wherein the personal care composition is in the form selected from: antiperspirants, deodorants, body washes, shower gels, bar soaps, shampoo, hair conditioners, and cosmetics.

1.33 Any of the preceding personal care compositions, wherein the personal care composition is an antiperspirant or deodorant in the form selected from: a roll-on, a gel, a cream, a stick, and an aerosol formulation.

1.34 The personal care composition of any of the preceding compositions, wherein the composition is free or substantially free of an aluminum antiperspirant agent/active, zirconium-based antiperspirant actives, zinc-based antiperspirant actives, non-oxalate titanium-based antiperspirant actives, iron-based antiperspirant actives, and/or magnesium-based antiperspirant actives. In some embodiments, the personal care composition may contain about 3 wt. % or less, about 2 wt. % or less, about 1 wt. % or less, about 0.5 wt. % or less, about 0.1 wt. % or less, about 0.05 wt. % or less, or about 0.01 wt. % or less of aluminum-based antiperspirant actives, magnesium-based antiperspirant actives, non-oxalate titanium-based antiperspirant actives, free-from zirconium-based antiperspirant actives, iron-based antiperspirant actives, and/or zinc-based antiperspirant actives (individually or cumulatively), based on the total weight of the personal care composition.

1.35 The personal care composition of any of the preceding compositions, wherein the composition is antiperspirant stick or aerosol, and wherein the antiperspirant stick or aerosol is anhydrous or substantially anhydrous.

In one aspect, the disclosure provides (i) a method (Method 1.0) for controlling perspiration comprising applying to a user's skin an antiperspirant effective amount of a formulation of any embodiment embraced or specifically described herein, e.g., any of Compositions 1 et seq; and (ii) a method for controlling odor from perspiration (Method 2.0) comprising applying to a user's skin a deodorant effective amount of a formulation of any embodiment embraced or specifically described herein, e.g., any of Compositions 1 et seq. Both Method 1.0 and Method 2.0 comprise reacting the metal oxalate (i.e., potassium oxalate and/or potassium titanium oxide oxalate) with endogenous calcium in a user's sweat in order to produce an insoluble precipitate that is able to block sweat glands and reduce or prevent sweat.

As used herein, the term "antiperspirant composition" is used to describe personal care compositions that function as antiperspirant compositions, deodorant compositions, or as dual-purpose antiperspirant-deodorant compositions.

As used herein, the term "substantially free" refers to compositions which contain no more than 0.5% by wt. of an ingredient, relative to the weight of the total composition (e.g., from 0.1-0.5 wt. %, of an aluminum containing active, based on the total weight of the personal care composition), zirconium-based antiperspirant actives, zinc-based antiperspirant actives, non-oxalate titanium-based antiperspirant actives, iron-based antiperspirant actives, and/or magnesium-based antiperspirant actives. In some embodiments, the personal care composition may contain about 3 wt. % or less, about 2 wt. % or less, about 1 wt. % or less, about 0.5 wt. % or less, about 0.1 wt. % or less, about 0.05 wt. % or less, or about 0.01 wt. % or less of aluminum-based antiperspirant actives, magnesium-based antiperspirant actives, non-oxalate titanium-based antiperspirant actives, free-from zirconium-based antiperspirant actives, iron-based antiperspirant actives, and/or zinc-based antiperspirant actives (individually or cumulatively), based on the total weight of the personal care composition.

As used herein, the term antiperspirant can refer to any material that can form a "plug" in a pore to reduce sweating, or antiperspirant refers to those materials classified as antiperspirants by the Food and Drug Administration under 21 CFR part 350. In some aspects, antiperspirants may also be deodorants.

As used herein, "personal care composition" is meant to include a composition for topical application to the skin of mammals, especially humans. The personal care composition is formulated into a product which can be applied to a human body for improving appearance, and/or cleansing and/or odor control and/or sweat reduction and/or general aesthetics.

As used herein, "potassium titanium oxalate" and "potassium titanium oxide oxalate" are used interchangeably and refer to compositions with a molecular formula of: $C_4K_2O_9Ti$ (CAS: 14481-26-6) or $C_4K_2O_9Ti \cdot 2H_2O$ (if in dihydrate form, CAS: 14402-67-6). As used herein, "potassium titanium oxalate" and "potassium titanium oxide oxalate" can both be abbreviated using the designation "KTO".

As used herein, "structurant", unless otherwise specified, refers to a material known in the art or otherwise effective in providing solidifying, gelling, and/or suspension properties to the composition, which provides structure to the final product form. The structurants may be a wax or a gelling agent. Structurant materials can include solids under ambient conditions and include wax (waxy materials), organic solids, modified silicone solids, crystalline or other gellants, or combinations thereof.

"Volatile", as used herein, means having a flash point of less than about 100° C. "Non-volatile", as used herein, means having a flash point of greater than about 100° C.

The antiperspirant active ingredients for use in the antiperspirant embodiments of the present disclosure include any compound, composition or other material having antiperspirant activity.

In one aspect, any of the compositions of the disclosure, e.g., any of Composition 1.0 et seq, can be any type of personal care composition. In certain embodiments, the composition is any composition in which it is desired to include an antibacterial agent for application to the skin. Examples of such compositions include, but are not limited to, personal care compositions, antiperspirants, deodorants, body washes, shower gels, bar soaps, shampoo, hair conditioners, and cosmetics.

In one aspect, any of the compositions of the disclosure, e.g., any of Composition 1.0 et seq, can be in the form of antiperspirant/deodorant compositions, and the carrier can be any carrier that is used for antiperspirants/deodorants. The carrier can be in the form of a stick, a gel, a roll-on, or an aerosol. For stick formulations, the carrier may include oils and/or silicones and gelling agents. An example of a formulation can be found in US2011/0076309A1, incorporated by reference herein.

In one aspect, optional ingredients that can be included in an antiperspirant and/or deodorant formulation of the compositions of the disclosure, e.g., any of Composition 1.0 et seq, include: solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments. If desired, an antiperspirant and/or deodorant agent additional to the antiperspirant active ingredient can be included, for example an odor reducing agent such as a sulfur precipitating agent, e.g., copper gluconate, zinc gluconate, zinc citrate, etc.

In one aspect, the personal care composition of the disclosure may include one or more polyol(s). Preferably, the personal care compositions include one or more polyol(s) in an amount from about 0.1 to about 25 wt. %, based on the total weight of the personal care composition. For example, the total amount of polyol(s) in the personal care composition may be from about 0.1 to about 22 wt. %, about 0.1 to about 18 wt. %, about 0.1 to about 12 wt. %, about 0.1 to about 8 wt. %, about 0.1 to about 6 wt. %, about 0.1 to about 4 wt. %, about 0.1 to about 3 wt. %, about 0.1 to about 2 wt. %; about 0.1 to about 1 wt. %; from about 0.5 to about 22 wt. %, about 0.5 to about 18 wt. %, about 0.5 to about 12 wt. %, about 0.5 to about 8 wt. %, about 0.5 to about 6 wt. %, about 0.5 to about 4 wt. %, about 0.5 to about 3 wt. %, about 0.5 to about 2 wt. %; about 0.5 to about 1 wt. %; from about 1 to about 22 wt. %, about 1 to about 18 wt. %, about 1 to about 12 wt. %, about 1 to about 8 wt. %, about 1 to about 6 wt. %, about 1 to about 4 wt. %, about 1 to about 3 wt. %, about 1 to about 2 wt. %; from about 2 to about 22 wt. %, about 2 to about 18 wt. %, about 2 to about 12 wt. %, about 2 to about 8 wt. %, about 2 to about 6 wt. %, about 2 to about 4 wt. %, about 2 to about 3 wt. %; from about 3 to about 22 wt. %, about 3 to about 18 wt. %, about 3 to about 12 wt. %, about 3 to about 8 wt. %, about 3 to about 6 wt. %; from about 5 to about 25 wt. %, about 5 to about 22 wt. %, about 5 to about 20 wt. %, about 5 to about 18 wt. %, about 5 to about 16 wt. %, about 5 to about 12 wt. %, about 5 to about 10 wt. %, about 5 to about 8 wt. %; from about 7 to about 25 wt. %, about 7 to about 22 wt. %, about 7 to about 20 wt. %, about 7 to about 18 wt. %, about 7 to about 16 wt. %; from about 9 to about 25 wt. %, about 9 to about 22 wt. %, about 9 to about 20 wt. %, about 9 to about 18 wt. %, about 9 to about 16 wt. %; from about 12 to about 25 wt. %, about 12 to about 22 wt. %, about 12 to about 20 wt. %, about 12 to about 18 wt. %, about 12 to about 16 wt. %; from about 14 to about 25 wt. %, about 14 to about 22 wt. %, about 14 to about 20 wt. %, about 14 to about 18 wt. %; from about 16 to about 25 wt. %, about 16 to about 22 wt. %, about 16 to about 20 wt. %; from about 18 to about 25 wt. %, about 21 to about 25 wt. %, or any range or subrange thereof, based on the total weight of the personal care composition.

The polyol(s) may be chosen from glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Polyols that may be included in the personal care composition, in certain instances, include ethylene glycol, propylene glycol, butylene glycol, hexylene glycol, glycerin, diglycerin, diethylene glycol, and dipropylene glycol, and mixtures thereof. In some cases, the personal care composition comprises glycerin, and optionally one or more polyols other than glycerin. Non-limiting examples of polyols that may, optionally, be included in the personal care composition and/or may be chosen from alkanediols such as glycerin, 1,2,6-hexanetriol, trimethylolpropane, ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propyleneglycol, butylene glycol, hexylene glycol, dipropylene glycol as well as alkyl ethers of diethylene glycol, e.g., monoethyl ether or monobutyl ether of diethylene glycol. In some cases, the one or more polyols may include or be chosen from ethylene glycol, propylene glycol, butylene glycol, hexylene glycol, pentylene glycol, 1,3-propanediol, diethylene glycol, dipropylene glycol, 1,4-butanediol, 1,5-pentanediol, hexane-1,6-diol, glycerin, diglycerin, caprylyl glycol, and/or a mixture of two or more thereof. In certain embodiments, the personal care composition may include polyol(s) selected from glycerin (preferably, vegetable refined glycerin), butylene glycol, and 1,3-propanediol, polyglutamic acid, saccharide isomerate, and combinations thereof. In some embodiments, the polyol is a polyethylene glycol, such as polyethylene glycol 600.

Additionally or alternatively, the personal care composition may include polyol(s) having a molecular weight of from about 100 to 5000 g/mol. For instance, the polyol may comprise a polyethylene glycol, a polypropylene glycol, a block polymer of polyethylene glycol and polypropylene glycol, or a combination of two or more thereof. In some embodiments, the polyol comprises a polypropylene glycol, a polypropylene glycol, and/or a block polymer of polyethylene glycol and polypropylene glycol having a molecular weight of about 100 to about 900, about 200 to about 800, about 400, about 1500 to about 2500, about 2000 to about 4500 or any range or subrange thereof.

In one aspect, the compositions of the disclosure, e.g., any of Composition 1.0 et seq, can also further comprise emollients in any desired amount to achieve a desired emollient effect. Emollients are known in the art and are used to impart a soothing effect on the skin. Classes of non-volatile emollients include non-silicone and silicone emollients. Non-volatile, non-silicone emollients include $C_{12-15}$ alkyl benzoate. The non-volatile silicone material can be a polyethersiloxane, polyalkyarylsiloxane or polyethersiloxane copolymer. An illustrative non-volatile silicone material is phenyl trimethicone. Non-limiting examples of emollients can be found in U.S. Pat. No. 6,007,799. Examples include, but are not limited to: glycerin, ethylhexyl glycerin, isododecane, sodium starch octenylsuccinate, C12-C15 alkyl benzoate, mineral oil, caprylyl glycol, PPG-14 butyl ether, PPG-3 myristyl ether, secondary alcohol ethoxylates (e.g. Tergitol sold by Dow Chemical Company, Midland, MI) stearyl alcohol, stearic acid and salts thereof, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl)adipate), Di-(2-ethyl hexyl)succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, and hydrocyethyl stearate amide.

The amount of emollient(s) in the personal care composition may be from about 0.1 to about 15 wt. %, based on the total weight of the personal care composition. For example, the total amount of emollient(s) in the personal care composition may be about 0.1 to about 15 wt. %, about 0.1 to about 12 wt. %, about 0.1 to about 9 wt. %, about 0.1 to about 6 wt. %, about 0.1 to about 4 wt. %, about 0.1 to about 2 wt. %; from about 0.5 to about 15 wt. %, about 0.5 to about 12 wt. %, about 0.5 to about 9 wt. %, about 0.5 to about 6 wt. %, about 0.5 to about 4 wt. %, about 0.5 to about 2 wt. %; from about 1 to about 15 wt. %, about 1 to about 12 wt. %, about 1 to about 9 wt. %, about 1 to about 6 wt. %, about 1 to about 4 wt. %, about 1 to about 2 wt. %; from about 2 to about 15 wt. %, about 2 to about 12 wt. %, about 2 to about 9 wt. %, about 2 to about 6 wt. %, about 2 to about 4 wt. %; from about 4 to about 15 wt. %, about 4 to about 12 wt. %, about 4 to about 9 wt. %, about 4 to about 6 wt. %; from about 7 to about 15 wt. %, about 7 to about 12 wt. %, about 7 to about 9 wt. %; from about 10 to about 15 wt. %, about 10 to about 12 wt. %, or about 12 to about 15 wt. %, including any range or subrange thereof, based on the total weight of the personal care composition.

In one aspect, the personal care composition may include one or more filler(s). The one or more filler(s) may be present in the personal care composition in an amount from about 1 to about 95 wt. %, based on the total weight of the personal care composition. For example, the total amount of filler in the personal care composition may be about 5 to about 95 wt. %, about 10 to about 95 wt. %, about 15 to about 95 wt. %, about 20 to about 95 wt. %, about 30 to about 95 wt. %, about 40 to about 95 wt. %, about 50 to about 95 wt. %, about 60 to about 95 wt. %, about 70 to about 95 wt. %, about 80 to about 95 wt. %, about 90 to about 95 wt. %; about 5 to about 90 wt. %, about 10 to about 90 wt. %, about 15 to about 90 wt. %, about 20 to about 90 wt. %, about 30 to about 90 wt. %, about 40 to about 90 wt.

%, about 50 to about 90 wt. %, about 60 to about 90 wt. %, about 70 to about 90 wt. %, about 80 to about 90 wt. %; about 5 to about 80 wt. %, about 10 to about 80 wt. %, about 15 to about 80 wt. %, about 20 to about 80 wt. %, about 30 to about 80 wt. %, about 40 to about 80 wt. %, about 50 to about 80 wt. %, about 60 to about 80 wt. %, about 70 to about 80 wt. %; about 5 to about 70 wt. %, about 10 to about 70 wt. %, about 15 to about 70 wt. %, about 20 to about 70 wt. %, about 30 to about 70 wt. %, about 40 to about 70 wt. %, about 50 to about 70 wt. %, about 60 to about 70 wt. %; about 5 to about 60 wt. %, about 10 to about 60 wt. %, about 15 to about 60 wt. %, about 20 to about 60 wt. %, about 30 to about 60 wt. %, about 40 to about 60 wt. %, about 50 to about 60 wt. %; about 5 to about 50 wt. %, about 10 to about 50 wt. %, about 15 to about 50 wt. %, about 20 to about 50 wt. %, about 30 to about 50 wt. %, about 40 to about 50 wt. %, including any ranges and subranges therebetween, based on the total weight of the personal care composition.

The filler(s) may comprise ethoxylated/propoxylated surfactants, such as PPG-14 butyl ether, or PEG-8-distearate, or mixtures of emollients some of which also have some surfactant character. The filler can be cornstarch, talcum powder (magnesium silicate), fumed silica, inorganic clays, polyethylene, or mixture of two or more thereof. Preferably, the inert filler, in particulate form, should have physical properties (e.g., size, shape, etc.) that are similar to those of the antiperspirant active material (e.g., antiperspirant active metal salt).

In one aspect, the compositions of the disclosure, e.g., any of Composition 1.0 et seq, can comprise a fragrance. Any known fragrance can be used in any desired amount. In one embodiment, the amount of fragrance is 0.01 to 10% by wt. of the total composition.

In one aspect, preservatives and/or antioxidants may be added to the compositions of the disclosure, e.g., any of Composition 1.0 et seq, to act as ingredient protectants and for maintenance of long-term stability of the composition. Examples of preservatives and/or antioxidants include, but are not limited to citric acid, sodium benzoate, sodium lactate, butylated hydroxytoluene, pentaerythrityl tetra-di-t-butyl hydroxyhydrocinnamate. In some cases, the preservative(s) may be selected from caprylyl glycol, phenoxyethanol, butylated hydroxytoluene, ethylenediaminetetraacetic acid, ethylhexylglycerin, citric acid, benzoic acid, a salt thereof, and combinations thereof. Additional examples of preservatives include lactic acid, sodium benzoate, sodium lactate, triethyl citrate, butylated hydroxytoluene, and pentaerythrityl tetra-di-t-butyl hydroxyhydrocinnamate, a salt thereof, or combinations thereof.

The personal care composition may comprise the preservative(s) in an amount from about 0.1 to about 7 wt. %, based on the total weight of the personal care composition. In some instances, the one or more preservative(s) is present in the personal care composition in a total amount from about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; from about 0.4 to about 7 wt. %, about 0.4 to about 6 wt. %, about 0.4 to about 5 wt. %, about 0.4 to about 4 wt. %, about 0.4 to about 3 wt. %, about 0.4 to about 2 wt. %, about 0.4 to about 1 wt. %; from about 0.8 to about 7 wt. %, about 0.8 to about 6 wt. %, about 0.8 to about 5 wt. %, about 0.8 to about 4 wt. %, about 0.8 to about 3 wt. %, about 0.8 to about 2 wt. %; from about 1.4 to about 7 wt. %, about 1.4 to about 6 wt. %, about 1.4 to about 5 wt. %, about 1.4 to about 4 wt. %, about 1.4 to about 3 wt. %; from about 2 to about 7 wt. %, about 2 to about 6 wt. %, about 2 to about 5 wt. %, about 2 to about 4 wt. %, about 2 to about 3 wt. %; from about 3 to about 7 wt. %, about 3 to about 6 wt. %, about 3 to about 5 wt. %; from about 4 to about 7 wt. %, about 4 to about 6 wt. %, about 5 to about 7 wt. %, or any range or subrange thereof, based on the total weight of the personal care composition.

In one aspect, the compositions of the disclosure, e.g., any of Composition 1.0 et seq, may also contain polymeric materials for thickening, such as polyamides, cellulose derivatives (e.g., hydroxypropylcellulose, hydroxypropyl methyl cellulose, etc.) and natural or synthetic gums (e.g., xanthan gum), such as polyglycerides including agar, agarose, pectin, or guars or mixtures or combinations thereof. One class of materials worthy of attention for thickening a water-immiscible phase comprises derivatives of hydrolysed starch or other polysaccharides, including in particular esterified dextrins, such as dextrin palmitate. A further class of polymers that can be included with any of C are particularly directed to structuring an oil phase containing a silicone oil comprises polysiloxane elastomers. Suspending agents such as silicas or clays such as bentonite, montmorillonite or hectorite, including those available under the trademark Bentone can also be employed to thicken liquid compositions according to the disclosure. The composition can be thickened with non-polymeric organic gellants, including selected dibenzylidene alditols (e.g., dibenzylidene sorbitol).

In one aspect, the personal care compositions of the disclosure may include one or more thickening agent(s). The total amount of thickening agent(s) in the personal care composition, if present, may be from about 0.1 to about 7 wt. %, about 0.1 to about 5 wt. %, about 0.1 to about 4 wt. %, about 0.1 to about 3 wt. %, about 0.1 to about 2 wt. %, about 0.1 to about 1 wt. %; from about 0.5 to about 7 wt. %, about 0.5 to about 5 wt. %, about 0.5 to about 4 wt. %, about 0.5 to about 3 wt. %, about 0.5 to about 2 wt. %, about 0.5 to about 1 wt. %; from about 1 to about 7 wt. %, about 1 to about 5 wt. %, about 1 to about 4 wt. %, about 1 to about 3 wt. %, about 1 to about 2 wt. %; from about 2 to about 7 wt. %, about 2 to about 5 wt. %, about 2 to about 4 wt. %, about 2 to about 3 wt. %; from about 3 to about 7 wt. %, about 3 to about 5 wt. %, about 3 to about 4 wt. %, or any range or subrange thereof, based on the total weight of the personal care composition.

Thickening agents may be referred to as "thickeners." Thickening agents are typically included to increase the viscosity of the personal care compositions. Non-limiting examples of thickening agents that may be incorporated into or excluded from the personal care compositions include natural gums, polyacrylate crosspolymers or cross linked polyacrylate polymers, cationic acrylate copolymers, anionic acrylic or carboxylic acid polymers, polyacrylamide polymers, polysaccharides such as cellulose derivatives, cationic gums, polyquaterniums, vinylpyrrolidone homopolymers/copolymers, $C_{8-24}$ hydroxyl substituted aliphatic acid, $C_{8-24}$ conjugated aliphatic acid, sugar fatty esters, polyglyceryl esters, and a mixture thereof. Particular types of thickening agents that may be mentioned include: gums (e.g., natural gums), sucrose esters, polyvinylpyrrolidone (PVP) and co-polymers, celluloses, polyquaternium compounds, and carboxylic acid or carboxylate based homopolymer or co-polymer, which can be linear or crosslinked.

The thickening agents may, also or alternatively, be chosen from xanthan gum, guar gum, biosaccharide gum, cellulose, acacia seneca gum, sclerotium gum, agarose, pectin, gellan gum, hyaluronic acid. In some instances, the thickening agent may be a gum, such as one or more selected from xanthan gum, sodium starch octenylsuccinate, hydroxypropyl starch phosphate, diutan gum, carrageenan, carboxymethylcellulose, cellulose gum, sclerotium gum, hydroxypropyl methylcellulose, and combinations thereof. Additionally, the thickening agents may include polymeric thickeners selected from the group consisting of ammonium polyacryloyldimethyl taurate, ammonium acryloyldimethyltaurate NP copolymer, acrylates copolymers, polyacrylamide, carbomer, and acrylates/$C_{10-30}$ alkyl acrylate crosspolymer, acrylates/beheneth-25 methacrylate copolymer, and a mixture thereof.

In certain cases, the personal care composition may comprise a thickening agent selected from thickening polymers, such as polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and/or starch derivatives (for example, starch oxide, dialdehyde starch, dextrin, British gum, acetyl starch, starch phosphate, carboxymethyl starch, hydroxyethyl starch, hydroxypropyl starch). In some embodiments, the thickening agent is selected from among hydroxypropyl methylcellulose, polyethylene glycols (PEGs), polyacrylic acids (sold under the name of Carbopol), cross-linked homopolymer of acrylic acid (sold under the name of Carbopol® Ultrez 30 polymer), and acrylates of $C_{10-30}$ alkyl acrylate crosspolymer (sold under the name of Carbopol® Ultrez 20 polymer).

In one aspect, the personal care compositions of the disclosure may include one or more structuring agent(s). The one or more structuring agent(s), if present, may be in an amount from about 0.5 to about 9 wt. %, based on the total weight of the personal care composition. For instance, the personal care composition may include one or more structuring agent(s) in an amount from about 0.5 to about 9 wt. %, about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1.5 wt. %, about 0.5 to about 1 wt. %; from about 1 to about 9 wt. %, about 1 to about 7 wt. %, about 1 to about 6 wt. %, about 1 to about 5 wt. %, about 1 to about 4 wt. %, about 1 to about 3 wt. %, about 1 to about 2 wt. %; from about 1.5 to about 9 wt. %, about 1.5 to about 7 wt. %, about 1.5 to about 6 wt. %, about 1.5 to about 5 wt. %, about 1.5 to about 4 wt. %, about 1.5 to about 3 wt. %, about 1.5 to about 2 wt. %; from about 2 to about 9 wt. %, about 2 to about 7 wt. %, about 2 to about 6 wt. %, about 2 to about 5 wt. %, about 2 to about 4 wt. %, about 2 to about 3 wt. %; from about 3 to about 9 wt. %, about 3 to about 7 wt. %, about 3 to about 6 wt. %, about 3 to about 5 wt. %, about 3 to about 4 wt. %; from about 4 to about 9 wt. %, about 4 to about 7 wt. %, about 4 to about 6 wt. %, about 4 to about 5 wt. %, or any range or subrange thereof.

Examples of structuring agents include waxes and/or gelling agents. The structuring agents may be a solid under ambient conditions, such as wax (waxy materials), organic solids, modified silicone solids, crystalline or other gellants, or combinations thereof. In certain embodiments, the structuring agent may be a gelling agent. Examples of structuring agents include waxes, esters of fatty acid and fatty alcohol, triglycerides, partially or fully hydrogenated soybean oil, partially or fully hydrogenated castor oil, other partial or fully hydrogenated plant oils, or other cosmetically acceptable materials (e.g., which are solid or semi-solid at room temperature and provide a consistency suitable for application to the skin) and combinations thereof. In some embodiments, the structuring agent(s) may be selected from Steareth-21, Steareth-10, Steareth-11, Steareth-13, Steareth-15, Steareth-20, Ceteareth-6, Ceteareth-7, Ceteareth-8, Ceteareth-9, Ceteareth-10, Ceteareth-11, and Ceteareth-12, polyglyceryl-6 palmitate/succinate mixture, glyceryl stearate, cetearyl alcohol (e.g., a 70/30 Stearyl/Cetyl Alcohol Blend), and a combination of two or more thereof.

In one aspect, any of the personal care composition of the disclosure is an antiperspirant/deodorant composition, e.g., any of Composition 1.0 et seq, and can be applied to axillary areas to reduce sweat and/or odor. The compositions can be applied by hand or via their packaging.

In still another aspect, the present disclosure relates to a method of administering any of Composition 1.0 et seq. for prophylaxis or reduction of skin irritation, a method for treatment of skin irritation, a method for reducing, eliminating or suppressing the irritating, preferably the skin-irritating, action of a substance or substance mixture, and a kit comprising (i) a formulation, a cosmetic product or a pharmaceutical product according to the present disclosure and, spatially separated, (ii) one or more substances or substance mixtures having an irritating, preferably a skin-irritating, action.

In another aspect, any of the compositions of the disclosure, e.g., any of Composition 1.0 et seq, can be an antiperspirant composition that is formulated into topical antiperspirant and/or deodorant formulations suitable for application to skin, illustratively a stick, a gel, a cream, a roll-on, a soft solid, a powder, a liquid, an emulsion, a suspension, a dispersion or a spray. Any of Composition 1.0, et seq can comprise a single phase or can be a multi-phase system, for example a system comprising a polar phase and an oil phase, optionally in the form of a stable emulsion. The composition can be liquid, semi-solid, or solid. The antiperspirant and/or deodorant formulation can be provided in any suitable container such as an aerosol can, tube or container with a porous cap, roll-on container, bottle, container with an open end, barrel, etc.

In one aspect, the compositions of the disclosure, e.g., any of Composition 1.0 et seq, can be used in a method to reduce sweating by applying the composition to skin. In certain embodiments, the application is to axilla. Also, the personal care compositions can be used to kill bacteria by bringing the bacteria into contact with the composition.

In some embodiments, the present invention provides a personal care composition comprising: an antiperspirant component comprising from about 0.1 wt. % to about 20 wt. % of a metal oxalate (including all weight ranges therebetween); and from about 1 wt. % to about 20 wt. % of an emollient system. In some embodiments, the present invention provides a personal care composition comprising: an antiperspirant component comprising from about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, or about 20 wt. %, of a metal oxalate.

In some embodiments, the metal oxalate comprises an alkali metal. In some embodiments, the alkali metal is selected from: Na, K, and Li. In other embodiments, the metal oxalate is selected from: potassium oxalate; potassium titanium oxalate; and a combination thereof.

In further embodiments, the personal care compositions described herein comprise from about 0.5 wt. % to about 7.5 wt. % of the metal oxalate.

In some embodiments, the personal care composition further comprises a cosmetically acceptable base comprising: a water-soluble alcohol; a glyceride; a medium to long chain organic acid, an alcohol; an ester; a thickener or gelling agent; an amino acid; a structurant; a fragrance; a dye; a pigment; and a combination of two or more thereof.

In other embodiments, the personal care composition further comprises an antioxidant and/or preservative selected from: citric acid; lactic acid; sodium benzoate; sodium lactate; triethyl citrate; butylated hydroxytoluene; pentaerythrityl tetra-di-t-butyl hydroxyhydrocinnamate; and a combination of two or more thereof.

In some embodiments, the personal care composition further comprises a gum blend comprising an ingredient selected from: xanthan gum, sodium starch octenylsuccinate; hydroxypropyl starch phosphate; and a combination of two or more thereof.

In some embodiments, the personal care composition is selected from a rinse-off or a leave-on composition. In other embodiments, the personal care composition is in a form selected from: an antiperspirant; a deodorant; a body wash; a shower gel; a bar soap; a shampoo; a hair conditioner; a lotion; and a cream.

Some embodiments of the present invention provide a method for inhibiting or preventing perspiration in a mammalian subject, comprising applying to a skin surface of a mammalian subject in need thereof, an effective amount of a composition described herein. In some embodiments, the metal oxalate is present in an amount effective to react with the mammalian subject's sweat to produce an insoluble precipitate. In some embodiments, the insoluble precipitate inhibits or prevents sweat production from a sweat gland.

Other embodiments of the present invention provide a personal care composition comprising: from about 0.5 wt. % to about 10 wt. % of potassium oxalate or potassium titanium oxalate; from about 10 wt. % to about 20 wt. % of glycerin; and from 0.5 wt. % to about 5 wt. % of isododecane. Yet other embodiments of the present invention provide a personal care composition according to claim 47, comprising: from about 0.5 wt. % to about 7.5 wt. % of potassium oxalate or potassium titanium oxalate; from about 12 wt. % to about 18 wt. % of glycerin; and 0.5%-3% by wt. of isododecane.

In some embodiments, the present invention provides a method for treating or preventing perspiration (e.g., treating hyperhidrosis) in a mammalian subject, comprising applying to a skin surface of a mammalian subject in need thereof, an effective amount of any one of the personal care compositions described herein.

The personal care compositions and formulations provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the disclosure extends to the product of the combination of the listed ingredients.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight relative to the total amount of the compositions.

Unless otherwise specifically identified, the ingredients for use in the compositions and formulations of the present disclosure are preferably cosmetically acceptable ingredients. As referred to herein, "cosmetically acceptable" means suitable for use in a formulation for topical application to human skin. A cosmetically acceptable excipient, for example, is an excipient which is suitable for external application in the amounts and concentrations contemplated in the formulations of this disclosure, and includes for example excipients which are "Generally Recognized as Safe" (GRAS) by the United States Food and Drug Administration.

The following examples further describe and demonstrate illustrative embodiments within the scope of the present disclosure. The examples are given solely for illustration and are not to be construed as limitations of this disclosure as many variations are possible without departing from the spirit and scope thereof. Various modifications of the disclosure in addition to those shown and described herein should be apparent to those skilled in the art and are intended to fall within the appended claims.

EXAMPLES

Example 1: Antiperspirant Formulas

TABLE A

| Material | Formula BB (wt. %) | Formula CC (wt. %) | Formula DD (wt. %) | Formula I (wt. %) |
| --- | --- | --- | --- | --- |
| Potassium Titanium Oxalate | 1 | 2 | 3 | 5 |
| Glycerin | 15 | 15 | 15 | 15 |
| Isododecane | 1 | 1 | 1 | 1 |
| Additional emollients | 0.68 | 0.68 | 0.68 | 0.68 |
| Preservative | 1.3 | 1.3 | 1.3 | 1.3 |
| Fructose | 0.01 | 0.01 | 0.01 | 0.015 |
| Glucose | 0.0075 | 0.0075 | 0.0075 | 0.0075 |
| Sucrose | 0.005 | 0.005 | 0.005 | 0.005 |
| Inulin | 0.225 | 0.225 | 0.225 | 0.225 |
| Antibacterial | 0.9 | 0.9 | 0.9 | 0.9 |
| Polyhydric alcohol | 0.5 | 0.5 | 0.5 | 0.5 |
| Gum Base Blend* | 2 | 2 | 2 | 2 |
| Calcium Silicate | — | — | — | 0.25 |
| Triethyl Citrate | 0.5 | 0.5 | 0.5 | — |
| Fragrance | 1.4 | 1.4 | 1.4 | 1.4 |
| Water | Q.S to 100 | Q.S to 100 | Q.S to 100 | Q.S to 100 |

*"Gum blend base" contains combination of: Xanthan Gum (1%), Sodium Starch Octenylsuccinate (0.75%) and Hydroxypropyl Starch Phosphate (0.25%).

Example 2: Back Screening Study to Observe Sweat Reduction Versus Untreated Site (Formulas with 5 wt. % Potassium Titanium Oxalate)

A back screening study is conducted to evaluate the performance and efficacy of different non-aluminum deodorant roll-on personal care compositions in accordance with aspects of the invention and compared them with current market deodorant roll-on personal care compositions. Non-aluminum personal care compositions containing glycerin, isododecane, triethyl citrate and potassium titanium oxalate were evaluated. Sweat was collected from twelve sites on the back at baseline and 24 hours after three 3 applications of the respective personal care composition.

Composition I (15 wt. % glycerin+1 wt. % isododecane and 5 wt. % potassium titanium oxalate (KTO)) delivered significantly more sweat protection (i.e., an enhancement in the sweat reduction) than the other gum blend personal care compositions (specifically, Comp. E, Comp. G, Comp. H, Comp. F, Comp. D) and the medium efficacy control. Composition I also performed at parity to the positive control, which contained an aluminum active. All gum blend base roll-on deodorant personal care compositions delivered greater than 20% sweat reduction (except for the placebo).

TABLE 1

Percent Sweat Reduction vs. Untreated Site

| Composition | Ingredients | % Reduction vs. Untreated Site | Statistical Group (p < 0.05) |
|---|---|---|---|
| Positive Control | Market product with aluminum active - roll on | 64.7 | a |
| I | Gum Blend Base** w/15% Glycerin + 1% IDD & 5% KTO | 57.8 | b |
| Positive Control (medium efficacy) | Market product with aluminum active - roll on | 43.8 | c |
| C | Non-Aluminum Roll-On Steareth Base w/15% Glycerin | 39.2 | c |
| B | Non-Aluminum Roll-On Steareth Base Placebo | 35.7 | c, d |
| A | Non-Aluminum Roll-on w/ 2.56% Glycerin | 26.9 | d, e |
| E | Non-Aluminum Roll-On Gum Blend Base w/15% Glycerin | 25.5 | e |
| G | Non-Aluminum Roll-On Gum Blend Base w/15% Glycerin + 1% IDD & TEC | 23.6 | e |
| H | Non-Aluminum Roll-On, Gum Blend Base w/10% Glycerin + 1% IDD & 0.5% TEC | 22.0 | e |
| F | Non-Aluminum Roll-On, Gum Blend Base w/15% Glycerin + 1% IDD | 21.9 | e |
| D | Non-Aluminum Roll-On, Gum Blend Base (Placebo) | 9.7 | f |

* "IDD": Isododecane
* "TEC": Triethyl Citrate
* Formula I described in Table II is described in Table A of Example 1.
** "Gum blend base" contains a combination of Xanthan Gum, Sodium Starch Octenylsuccinate & Hydroxypropyl Starch Phosphate.

TABLE 1a

Ingredients for Formulas Listed in Table 1

| Ingredients | B (wt. %) | F (wt. %) | G (wt. %) | H (wt. %) |
|---|---|---|---|---|
| DEMINERALIZED WATER | Q.S. to 100 | Q.S. to 100 | Q.S. to 100 | Q.S. to 100 |
| STEARETH-2 | 5.04 | | | |
| PPG-15 STEARYL ETHER | 4.38 | | | |
| Preservative | 1.9 | 1.9 | 1.9 | 1.9 |
| STEARETH-21 | 1.26 | | | |
| Fragrance | 1.10 | 1.1 | 1.1 | 1.1 |
| Antibacterial | 1.0 | 1.0 | 1.0 | 1.0 |
| Additional Emollients | 1.7 | 1.7 | 1.7 | 1.7 |
| Polyhydric Alcohol | 0.5 | 0.5 | 0.5 | 0.5 |
| Fragrance | 0.3 | 0.3 | 0.3 | 0.3 |
| Inulin | 0.25 | 0.25 | 0.25 | 0.25 |
| Thickener | 0.2 | 0.2 | 0.20 | 0.2 |
| Glycerin | | 15.0 | 15.0 | 10.0 |
| Xanthan Gum | | 1.0 | 1.0 | 1.0 |
| Thickener | | 1.0 | 1.0 | 1.0 |
| Triethyl Citrate | | | 0.5 | 0.5 |
| Total Components | 100 | 100 | 100 | 100 |

| Ingredients | A (wt. %) | D (wt. %) | E (wt. %) | C (wt. %) | Positive Control (Medium Efficacy) (wt. %) |
|---|---|---|---|---|---|
| DEMINERALIZED WATER | Q.S. to 100 | Q.S. to 100 | Q.S. to 100 | Q.S. to 100 | Q.S. to 100 |
| STEARETH-2 | 4.34 | | | 5.04 | 2.3 |
| PPG-15 STEARYL ETHER | 4.38 | | | 4.38 | 1.56 |
| Preservative | 1.9 | 1.9 | 1.9 | 1.9 | |
| STEARETH-21 | 1.28 | | | 1.26 | |
| Fragrance | 1.4 | 1.4 | 1.4 | 1.4 | 1.2 |
| Antibacterial | 1.0 | 1.0 | 1.0 | 1.0 | |
| Additional Emollient(s) | 0.5 | 0.7 | 0.7 | 0.5 | |

TABLE 1a-continued

| Ingredients for Formulas Listed in Table 1 | | | | | |
|---|---|---|---|---|---|
| Polyhydric alcohol | 0.2 | 0.5 | 0.5 | 0.5 | |
| Inulin | 0.25 | 0.25 | 0.25 | 0.25 | |
| Thickener | 0.2 | 0.2 | 0.2 | 0.2 | |
| Glycerin | 2.56 | | 15.0 | 15.0 | |
| Xanthan Gum | | 1.0 | 1.0 | | |
| Thickener | | 1.0 | 1.0 | | |
| ALUMINUM CHLOROHYDRATE SOLUTION IN WATER | | | | | 30.12 |
| Emollient with BHT | | | | | 3.0 |
| Steareth-20 | | | | | 1.2 |
| Emollient | | | | | 0.3 |
| EDTA (62% Solution) | | | | | 0.25 |
| DI-TERTIARY BUTYL-PARA-CRESOL (BHT) | | | | | 0.05 |
| Total Components | 100 | 100 | 100 | 100 | 100 |

Table 2 demonstrates the percent sweat reduction that is generated for various prototypes compared to each base versus their representative placebo:

TABLE 2

| Composition Comparison* | % Sweat Reduction vs. Placebo |
|---|---|
| Steareth Base Comparison | |
| C vs B | 5.8 |
| Gum Base Comparison** | |
| I vs D | 114.1 |
| E vs D | 21.1 |
| G vs D | 18.2 |
| H vs D | 15.8 |
| F vs D | 15.6 |

*Formulas refer to those listed in Table 1 above
**Gum Blend contains combination of Xanthan Gum, Sodium Starch Octenylsuccinate & Hydroxypropyl Starch Phosphate As demonstrated in Table 2, the personal care compositions with a gum base demonstrated increased sweat reduction versus placebo as compared to the steareth base formula compared to the placebo. Moreover, Composition I (having 5 wt. % of potassium titanium oxide oxalate) demonstrated roughly a five-fold (about 500%) increase in sweat reduction (vs. placebo) as compared to Compositions E, G, H, and F which contain a non-aluminum active, which was not KTO.

Example 3: Back Screening Study to Observe Sweat Reduction Versus Untreated Site (Formulas with 1 wt. %, 2 wt. %, or 3 wt. % Potassium Titanium Oxalate)

A back screening study was conducted to evaluate the performance and efficacy of different non-aluminum deodorant roll-on base personal care compositions and compared them with current market deodorant roll-on personal care compositions. The non-Aluminum personal care compositions contained glycerin, isododecane, triethyl citrate, and potassium titanium oxalate are evaluated. Sweat was collected from twelve sites on the back at baseline and 24 hours after three 3 applications of the respective personal care composition.

Composition DD (having 3 wt. % of KTO) performed significantly better with respect to sweat reduction than Composition CC (having 2 wt. % of KTO) and Composition BB (1 wt. % of KTO). Furthermore, Composition CC (2 wt. % of performed significantly better with respect to sweat reduction than Composition BB (1 wt. % of KTO). Additionally, KTO Compositions CC and DD (2% and 3% KTO, respectively) performed significantly better with respect to sweat reduction as compared to the market deodorant roll-on personal care compositions having a magnesium active (Composition AA), the medium efficacy control, and the placebo.

TABLE 3

| | Percent Sweat Reduction vs. Untreated Site | | |
|---|---|---|---|
| Formula | Ingredients | % Reduction vs. Untreated Site | Statistical Group ($p < 0.05$) |
| Positive Control | Market product with aluminum active - roll on | 48.8 | a |
| Comp. DD | **Non-Aluminum Roll-On + 3% KTO | 48.2 | a |
| Comp. CC | **Non-Aluminum Roll-On + 2% KTO | 41.4 | b |
| Comp. BB | **Non-Aluminum Roll-On + 1% KTO | 30.3 | c |
| Positive Control (medium efficacy) | *Market product with aluminum active - roll on | 29.3 | c, d |
| Comp. II | Non-Aluminum Roll-On – Placebo | 27.1 | c, d, e |
| Comp. HH | Non-Aluminum Roll-On + 0.5% | 25.9 | c, d, e |
| Comp. GG | Non-Aluminum Roll-On + 2% Biomimetic HAP powder | 25.5 | c, d, e, f |
| Comp. EE | Non-Aluminum Roll-On + 2% MgCl2 | 21.0 | d, e, f |
| Comp. FF | Non-Aluminum Roll-On + 2% | 18.0 | e, f |
| Comp. AA | Market Product with magnesium active | 16.2 | f |

*Referenced in Table 1a
**Referenced in Table 1

TABLE 3a

Lists of Ingredients for Formulas referenced in Table 3:

| Ingredients | Comp. FF (wt. %) | Comp. GG (wt. %) | Comp. HH (wt. %) | Comp. EE (wt. %) |
|---|---|---|---|---|
| Demineralized Water | To Balance Q.S. to 100 | Q.S. to 100 | Q.S. to 100 | Q.S. to 100 |
| Glycerin | 15 | 15 | 15 | 15 |
| Magnesium Hydroxide (and) Magnesium Carbonate Hydroxide | 2 | | | |
| Preservative | 1.9 | 1.9 | 1.9 | 1.9 |
| Fragrance | 1.4 | 1.4 | 1.4 | 1.4 |
| Xanthan Gum | 1 | 1 | 1 | 1 |
| Thickener | 1 | 1 | 1 | 1 |
| Antibacterial | 1 | 1 | 1 | 1 |
| Emollient | 1 | 1 | 1 | 1 |
| Emollient | 0.5 | 0.5 | 0.5 | 0.5 |
| Triethyl Citrate | 0.5 | 0.5 | 0.5 | 0.5 |
| Polyhydric Alcohol | 0.5 | 0.5 | 0.5 | 0.5 |
| Inulin | 0.25 | 0.25 | 0.25 | 0.25 |
| Emollient | 0.2 | 0.2 | 0.2 | 0.2 |
| Biomimetic Hydroxyapatite Powder Functionalized with divalent cations (e.g., zn, mg, etc.) with Clay Minerals & Zinc PCA | | 2.0 | 0.5 | |
| Magnesium Chloride hexahydrate | | | | 2.0 |
| Total Components | 100.0 | 100.0 | 100.0 | 100.0 |

| Ingredients | Comp. II (wt. %) |
|---|---|
| Demineralized Water | Q.S. to 100 |
| Glycerin | 15.0 |
| Magnesium Hydroxide (and) Magnesium Carbonate Hydroxide | — |
| Sodium Lactate | 1.5 |
| Fragrance | 1.1 |
| Xanthan Gum | 1.0 |
| Thickener | 1.0 |
| Preservative | 1.0 |
| Additional Emollient(s) | 1.0 |
| Emollient | 0.5 |
| Triethyl Citrate | 0.5 |
| Polyhydric Alcohol | 0.5 |
| Preservative | 0.4 |
| Fragrance | 0.3 |
| Inulin | 0.25 |
| Emollient | 0.2 |

Example 4: Thermal Imaging and In Vivo Analysis

Sweat Production Analysis—Thermal Imaging Studies

A thermal imaging study was conducted to further evaluate the performance and efficacy of different non-aluminum deodorant roll-on base personal care compositions in accordance with aspects of the invention and compared to current market deodorant roll-on personal care compositions. This indirect imaging methodology allows the sweat protection benefits of the personal care compositions to be understood by better simulating their performance under real-life conditions. The baseline is first collected by performing aerobic exercise in a 100% cotton T-shirt. Immediately afterwards, the T-shirt is collected and the sweat retained is recorded using the thermal camera. On the following day, a test product is applied to the left side of the underarm at least 2 hours prior to exercising and the T-shirt is imaged.

A comparison of personal care compositions with 0 wt. % of KTO, 2 wt. % of KTO, 5 wt. % of KTO, and commercial personal care compositions with a magnesium active, demonstrated that the personal care compositions with 2 wt. % of KTO and 5 wt. % of KTO exhibited a decreased sweat production (an enhancement in the reduction of sweat) relative to the personal care compositions with no KTO or that had a magnesium active, as seen in Table 4.

TABLE 4

| Composition | Ingredients | % Sweat Produced |
|---|---|---|
| AA* | Market product with magnesium active - Roll-On | 79% |
| II** | Non-Aluminum Roll-On + 0% KTO (placebo) | 125% |
| CC**** | Non-Aluminum Roll-On + 2% KTO | 61% |
| I*** | Non-Aluminum Roll-On + 5% KTO | 44% |

*As described in Table 3
**As described in Table 3a
***As described in Table A

Pore Activation Analysis—In Vivo Thermal Imaging

A pore activation study was conducted to demonstrate the ability of the non-aluminum deodorant roll-on base personal care compositions in accordance with aspects of the invention to inhibit the production of sweat. The observed behaviors were benchmarked against the current market deodorant roll-on personal care compositions. In this direct imaging methodology, the personal care compositions were applied onto the forehead of individuals and the drying time was varied, as this will modify the time for the active ingredient to be internalized into the skin. Next, the degree of internalization was tested by performing aerobic exercises and the region of the forehead where the personal care composition was applied onto the skin was imaged.

Figure 1B:
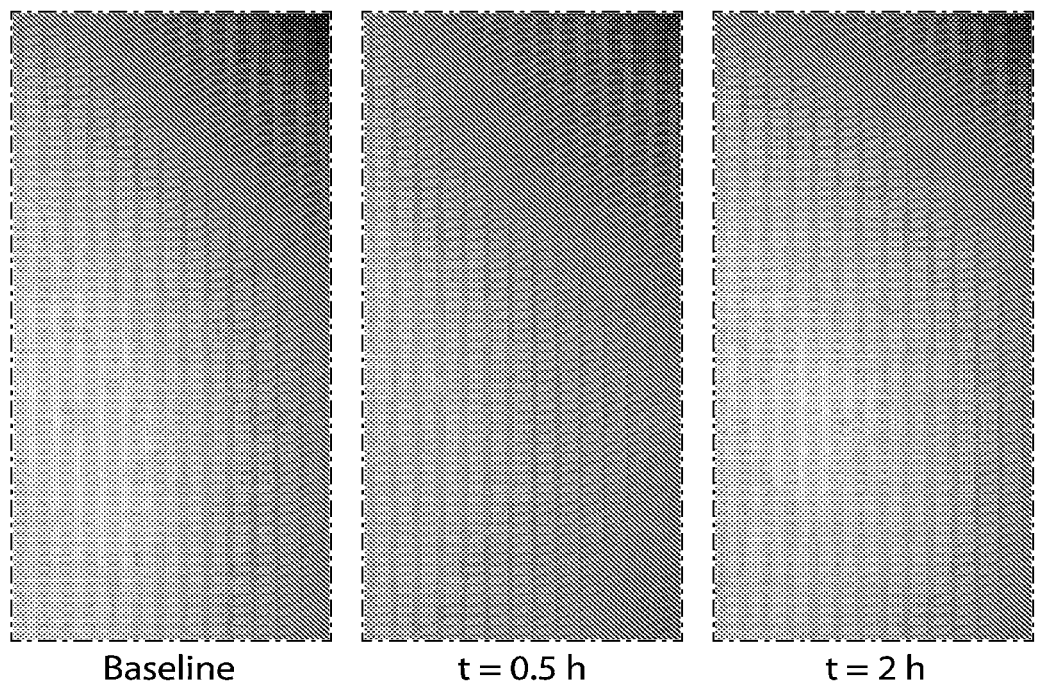
FIG. 1B is a thermal image demonstrating the lack of pore activation on the skin from the application of a comparative personal care composition that contains magnesium active instead of potassium titanium oxide oxalate over a time course of two hours.

Comparison of the Compositions with 5 wt. % of KTO, and the market deodorant roll-on personal care compositions with a magnesium active, demonstrated that no observable pore activation in the potassium titanium oxide oxalate ("KTO") formula after 2 hours. Furthermore, no pore activation was demonstrated in the market formulation with a magnesium active at 0.5 hours. While the internalization process for the KTO active is slower than the magnesium active, without being bound by theory, this effectively illustrates that when KTO is absorbed into the skin it is capable of blocking the sweat pore. For example, this was demonstrated in FIG. 1.

Crystal Formation Analysis—In Vivo Digital Imaging

Digital imaging studies confirmed crystal formation with the application of the personal care compositions comprising 5 wt. % of potassium titanium oxalate.

A solubility study is performed in order to identify the optimal total composition of potassium titanium oxide oxalate in the formula. A light layer of the formulation was applied onto the right index finger of the subject and a digital microscope setup was used to image the applied area. Similar configurations have been utilized to study changes in the dimensions of large particles. This approach was adapted to study the presence of residual crystals not solubilized in the formulation.

Comparison of the personal care compositions having 0 wt. % of KTO, 2 wt. % of KTO, and 5 wt. % of KTO demonstrated that at concentrations of <2 wt. % of KTO, complete solubilization of KTO was observed. As the solubility limit is approached, KTO crystals (~μm) appear to leach out of the personal care composition, which was evident at 5%.

While the present disclosure has been described with reference to embodiments, it will be understood by those skilled in the art that various modifications and variations may be made therein without departing from the scope of the present disclosure as defined by the appended claims.

What is claimed is:

1. A personal care composition comprising:
   an antiperspirant component comprising from about 0.1 wt. % to about 20 wt. % of a metal oxalate comprising potassium titanium oxalate; and
   from about 1 wt. % to about 20 wt. % of an emollient system comprising glycerin and isododecane, wherein the weight percentages for the metal oxalate and the emollient system are based on the total weight of the personal care composition.

2. The personal care composition according to claim 1, wherein the metal oxalate further comprises potassium oxalate.

3. The personal care composition according to claim 1, comprising from about 0.5 wt. % to about 7.5 wt. % of the metal oxalate based on the total weight of the personal care composition.

4. The personal care composition according to claim 1, wherein the emollient system further comprises ethylhexyl glycerin, sodium starch octenylsuccinate, $C_{12}$-$C_{15}$ alkyl benzoate, mineral oil, caprylyl glycol, dimethicone, dicaprylyl ether, ethyl trisiloxane, PPG-14 butyl ether, PPG-3 myristyl ether, secondary alcohol ethoxylates, stearyl alcohol, stearic acid and salts thereof, glyceryl monoricinoleate, isobutyl palmitate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl stearate, Di-(2-ethyl hexyl)adipate, Di-(2-ethyl hexyl)succinate, isopropyl myristate, isopropyl palmitate, isopropyl stearate, octacosanol, butyl stearate, polyethylene glycols, oleic acid, triethylene glycol, lanolin, castor oil, acetylated lanolin alcohols, acetylated lanolin, petrolatum, isopropyl ester of lanolin, fatty acids, butyl myristate, isostearic acid, palmitic acid, PEG-8 distearate, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide, or a combination of two or more thereof.

5. The personal care composition according to claim 1, further comprising a cosmetically acceptable base selected from the group consisting of a water-soluble alcohol; a glyceride; a fatty acid, an alcohol; an ester; a thickener or gelling agent; an amino acid; a structurant; a fragrance; a dye; a pigment; and a combination of two or more thereof.

6. The personal care composition according to claim 1, further comprising citric acid, lactic acid, sodium benzoate, sodium lactate, triethyl citrate, butylated hydroxytoluene, pentaerythrityl tetra-di-t-butyl hydroxyhydrocinnamate, or a combination of two or more thereof.

7. The personal care composition according to claim 1, further comprising a prebiotic selected from: inulin, glucose, fructose, sucrose, or a combination of two or more thereof.

8. The personal care composition according to claim 1, further comprising a gum blend comprising xanthan gum, sodium starch octenylsuccinate, hydroxypropyl starch phosphate, or a combination of two or more thereof.

9. The personal care composition according to claim 8, wherein the gum blend comprises xanthan gum.

10. The personal care composition according to claim 1, wherein the personal care composition is selected from a rinse-off or a leave-on composition.

11. The personal care composition according to claim 1, wherein the personal care composition is in a form of an antiperspirant, a deodorant, a body wash, a shower gel, a bar soap, a shampoo, a hair conditioner, a lotion, a cream, or a combination thereof.

12. The personal care composition according to claim 1, wherein the personal care composition is substantially free of aluminum.

13. The personal care composition according to claim 1, wherein the personal care composition is free of aluminum.

14. The personal care composition according to claim 1, wherein the antiperspirant component consists essentially of the metal oxalate.

15. A method for inhibiting perspiration in a mammalian subject, comprising applying to a skin surface of a mammalian subject in need thereof, an effective amount of a personal care composition according to claim 1.

16. The method according to claim 15, wherein the method reduces sweat by about 20% or more.

17. The method according to claim 16, wherein an insoluble precipitate inhibits sweat production from a sweat gland.

18. The personal care composition according to claim 1, wherein the antiperspirant component consists of the metal oxalate.

19. A method for inhibiting perspiration in a mammalian subject, comprising applying to a skin surface of a mammalian subject in need thereof, an effective amount of a personal care composition according to claim 18.

\* \* \* \* \*